United States Patent [19]

Benderev

[11] Patent Number: 5,782,745
[45] Date of Patent: Jul. 21, 1998

[54] DEVICES AND METHODS FOR ASSESSMENT AND TREATMENT OF URINARY AND FECAL INCONTINENCE

[76] Inventor: Theodore V. Benderev, 26975 Magnolia Ct., Laguna Hills, Calif. 92653

[21] Appl. No.: 558,642

[22] Filed: Nov. 13, 1995

[51] Int. Cl.[6] ........................ A61F 2/00
[52] U.S. Cl. ................... 600/30; 128/DIG. 25
[58] Field of Search .............. 600/29–32; 128/DIG. 25

[56] References Cited

U.S. PATENT DOCUMENTS

| | | | |
|---|---|---|---|
| 5,437,649 | 8/1995 | Letchworth | 600/32 |
| 5,483,976 | 1/1996 | McLaughlin et al. | 600/32 |
| 5,513,660 | 5/1996 | Simon et al. | 600/32 |

*Primary Examiner*—John P. Lacyk
*Attorney, Agent, or Firm*—Stetina Brunda Garred & Brucker

[57] ABSTRACT

A device and method for evaluating and treating urinary as well as fecal incontinence by using proprioceptive neuromuscular facilitation. The device is adapted to be inserted within and retained within an anatomical passageway and provide periodic stimulus to wall or muscles within the anatomic passageway by way of pressure, stretching, resistance, vibration, and/or heat. The frequency, duration, and extent of the stimulus may be varied as desired for exercise regimens.

28 Claims, 2 Drawing Sheets

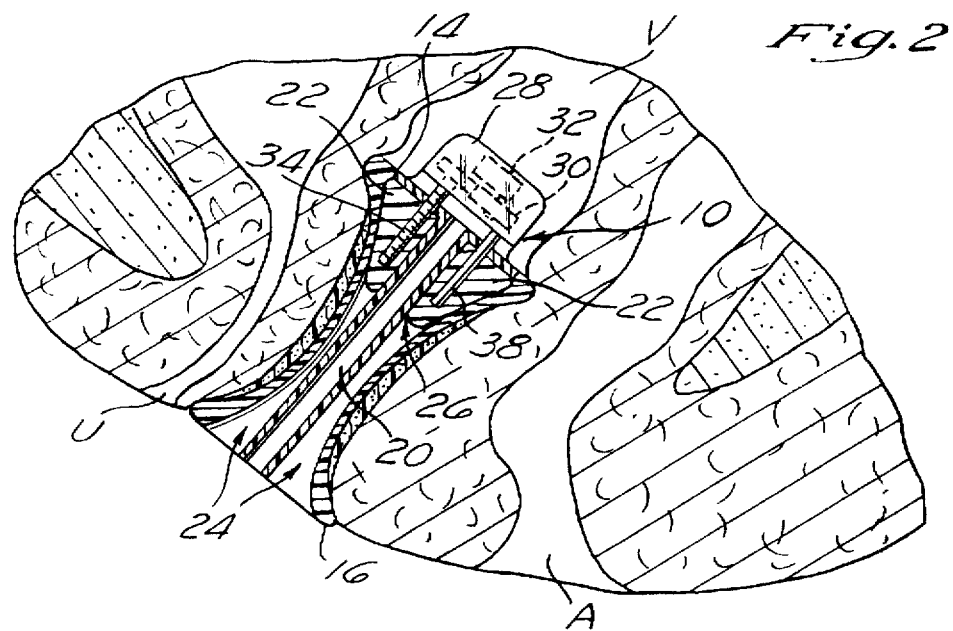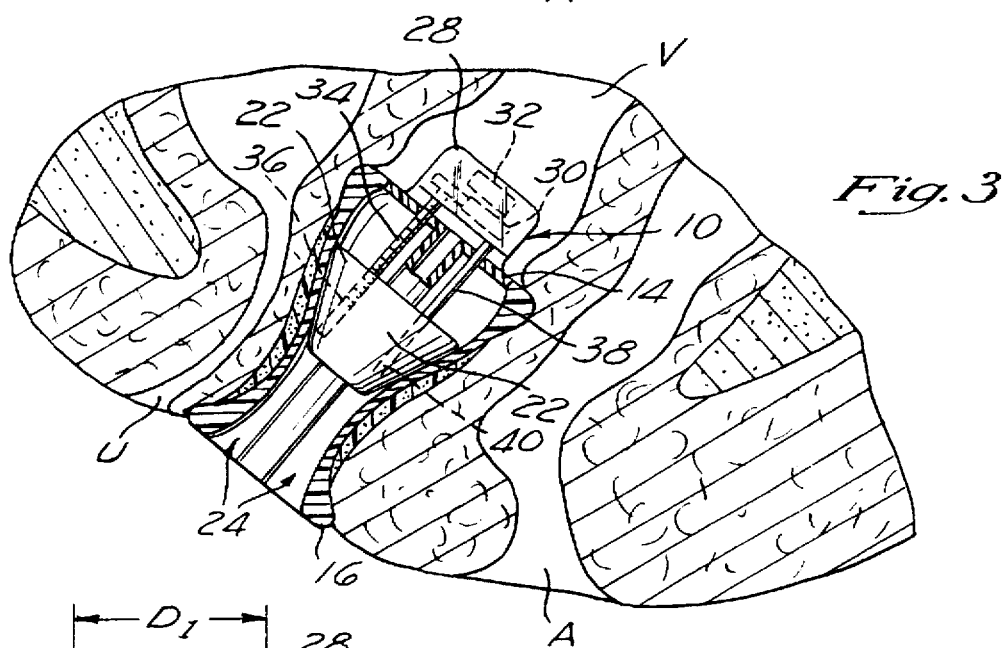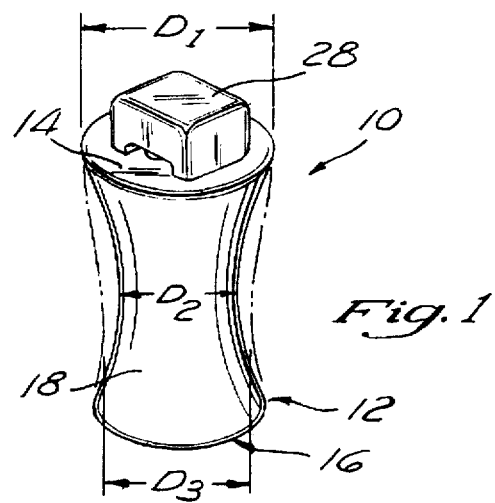

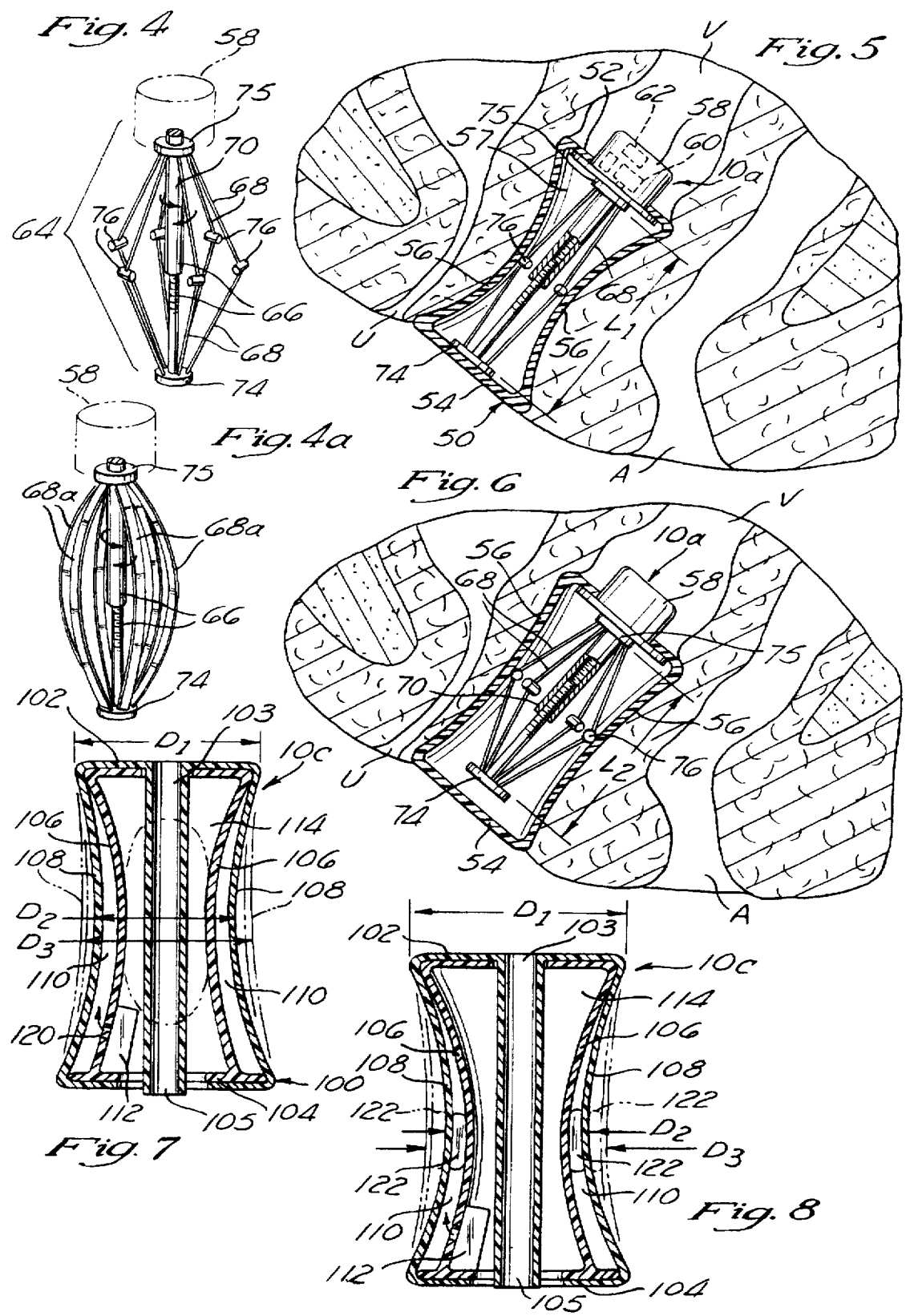

DEVICES AND METHODS FOR ASSESSMENT AND TREATMENT OF URINARY AND FECAL INCONTINENCE

FIELD OF THE INVENTION

The present invention relates generally to medical devices and methods, and more particularly to devices and methods for evaluating and treating urinary as well as fecal incontinence by using proprioceptive neuromuscular facilitation.

BACKGROUND OF THE INVENTION

Urinary incontinence is believed to affect 15% to 30% of noninstitutionalized persons over the age of 60, and more then 50% of elderly persons (over the age of 60) who reside in nursing homes.

The presently available modes of treatment for urinary incontinence fall into four general categories, namely: i) management apparatus, ii) behavioral, iii) pharmacologic, and iv) surgical.

i. Management Apparatus For Incontinence

The management apparatus modes of treatment generally comprise absorbent and/or catheter structures worn by a user to retain any urinary and/or fecal incontinence. In their simplest forms, such devices comprise diaper-like structures which must be periodically changed by the user. Although such management apparatus has proven generally effective in masking the results of incontinence, they are uncomfortable to wear, difficult to change, and oftentimes fail during use thereby embarrassing the user.

ii. Behavioral Treatment For Incontinence

The use of behavioral training as a treatment for urinary and/or fecal incontinence can involve numerous behavioral techniques including; bladder re-training (e.g., voiding on a timed schedule), and/or the performance of exercises (e.g., Kegel exercises) to strengthen and retrain a group of muscles collectively known as the "pelvic floor muscles". As an adjunct to these behavioral training techniques, various intravaginal and/or intra-anal devices may be utilized to facilitate the performance of such pelvic muscle training exercises. Such intravaginal and/or intra-anal devices have included simple pressure-exerting or weighted apparatus such as pessaries or intravaginal cones. Exemplary of such prior art pessaries are the pessaries manufactured by Milex Wester Company, 639 North Fairfax, Los Angeles, Calif. 90036; while an example of such weighted cone device is the "FEMINA" cone manufactured by Dacomed Corporation, 1701 East 79th Street, Minneapolis, Minn., 55425. Other types of prior art devices include electromyographic (EMG) transducers or sensors which are insertable into or placed just outside of the vagina and/or anus to obtain EMG data indicative of baseline pelvic floor muscle tone and/or contraction(s) of the pelvic floor muscles during the performance of specific muscle contraction exercises. Such EMG data may be usable for diagnostic purposes as well as for monitoring the performance and/or effect of muscle training exercises. Some EMG devices have included means for providing visual or auditory feedback to assist the patient in the performance of pelvic floor muscle exercises (e.g., Myoexorciser III, available from Verimed 1401 East Broward Boulevard, Suite 200, Fort Lauderdale, Fla. 33301 and the PRS 8900 Office System made by Incare Medical Products, Libertyville, Ill. 60048.

Additionally, the prior art has included at least one transvaginal electrical stimulation device which is operative to deliver periodic or timed electrical stimulation to the pelvic floor muscles and nerves. Such electrical stimulation causes involuntary contraction of the pelvic floor muscles and may serve as an adjunct to the performance of volitional exercise and/or other behavioral training techniques (e.g., Microgyn II Stimulation Device, InCare Medical Products, Division of Hollister Incorporated, 2000 Hollister Drive, LibertyVille, Ill., 60048 and also the Innova Feminine Incontinence Treatment System available from EMPI, Inc., 1275 Grey Fox Road, St. Paul, Minn. 55112).

Although some of or all of the above-described devices and systems for exercise and/or training of the pelvic floor muscles may be effective in the treatment of urinary incontinence, there remains a need for the development of improved devices and systems which are capable of strengthening and training the pelvic floor muscles in minimal time, with minimal assistance from physicians or other health care professionals as well as a system which serves to remind a user to perform muscle exercises and to provide proprioceptive input to assist the user in exercising and strengthening desired muscles.

iii. Pharmacologic Treatment For Incontinence

The prior art pharmacologic treatment of urinary incontinence typically involves the long term administration of drugs. Such pharmacologic treatment may result in drug-related side effects. Also, the efficacy of such pharmacologic treatment is frequently limited and largely dependant upon the patient's ability or willingness to comply with the prescribed drug dosage schedule.

iv. Surgical Treatment For Incontinence

The prior art surgical modes of treatment of urinary incontinence typically involve the performance of one or more major surgeries procedures under anesthesia. These major surgical procedures can be associated with significant risks and may sometime result in post-surgical failure, infections, or other complications. Also, these surgical procedures typically result in significant expense to the patient and/or the patient's third party insurer.

As such, there exists a substantial need in the art for an incontinence treatment system and methodology which reduces or eliminates the need for prior art management apparatus and/or surgical treatments, reduces the use of long-term drug administration, accentuates muscle strengthening and training while reminding a patient to conduct muscle strengthening exercise, as well as provide a proprioceptive input to assist the patient in contracting the appropriate muscles and/or muscle groups necessary for the effective treatment of incontinence.

SUMMARY OF THE INVENTION

In accordance with the present invention, there is provided a device which is insertable into a pelvic anatomical passageway of a patient (e.g., the vagina or anus) to facilitate the performance of pelvic muscle exercises. The device generally comprises a device body which is alternately transitionable between i) a rest mode configuration wherein said device body exerts no more than a base line amount of pressure against a predetermined region of the anatomical passageway within which the device body is located and, ii) an exercise mode configuration wherein the device body exerts more than the base line amount of pressure against the predetermined region of the anatomical passageway within which the device body is inserted. A small battery and battery-powered motor may be mounted on or within the device to drive the transformation of the device between the rest mode configuration and the exercise mode configuration. Additionally, a timer apparatus may be mounted on or within the device to trigger and control the timing, duration, repetitions, and frequency of transformation of the device between the rest mode configuration and the exercise mode configuration, on a predetermined time schedule.

Further in accordance with the invention, a vibrator apparatus may be mounted on or within the device to cause at least a portion of the device to vibrate in an exercise mode configuration.

Still further in accordance with the invention, a remote controlled triggering device may be used in addition to, or in place of, a timer or other control apparatus mounted on or within the device. Such remote control apparatus may be utilized to trigger, control and/or schedule all operational parameters of transformation of the device, back and forth, between its rest mode configuration and exercise mode configuration, from a remote location.

Still further in accordance with the invention, there is provided a method of treating urinary and/or fecal incontinence in a patient. In general, the method comprises the steps of inserting a device of the forgoing character into either the vagina or anus, and utilizing the device to intermittently deliver increased stretch/resistance/vibration/pressure or heat stimuli against the wall and/or adjacent muscles of the vagina or anus to facilitate the performance of pelvic muscle strengthening exercises by the patient in whom the device is inserted.

BRIEF DESCRIPTION OF THE DRAWINGS

FIG. 1 is a perspective view of a first embodiment of an indwelling urinary and/or fecal incontinence treatment device of the present invention.

FIGS. 2 is a cross sectional view of the device of FIG. 1 disposed in a resting mode and operatively inserted in to the vagina.

FIG. 3 is a cross sectional view of the device of FIG. 1 disposed in exercise mode and operatively inserted into the vagina.

FIG. 4 is a perspective view of an alternative second embodiment of the indwelling urinary and/or fecal incontinence treatment device of the present invention.

FIG. 4a is a perspective view of an alternative embodiment of the incontinence treatment device of FIG. 4.

FIG. 5 is a cross sectional view of the device of FIG. 4 disposed in a resting mode and operatively inserted into the vagina.

FIG. 6 is a cross sectional view of the device of FIG. 4 disposed in an exercise mode and operatively inserted into the vagina.

FIG. 7 is a cross sectional view of an alternative third embodiment of the indwelling incontinence treatment device of the present invention.

FIG. 8 is a cross sectional view of the device of FIG. 7 further equipped with an optional vibrator and/or heater apparatus.

DETAILED DESCRIPTION OF THE PREFERRED EMBODIMENTS

The following detailed description and the accompanying drawings are provided for the purpose of describing certain presently preferred embodiments of the invention only, and are not intended to limit the scope of the claimed invention in any way.

Some of the accompanying drawings include showings of the device of the present invention operatively positioned within the human body. The anatomical structures shown on such drawings are labeled in accordance with the following legend:

| | |
|---|---|
| Urethra | U |
| Vagina | V |
| Anus | A | i. First Embodiment

FIG. 1 shows a first embodiment of a intra-vaginal or intra-anal device 10 of the present invention which may be utilized for the effective treatment of both urinary and fecal incontinence in female as well as male users or patients. The device 10 is operative to provide timed or periodic changes in stimuli such as pressure or resistance against the pelvic floor muscles. The changes in pressure, stretch, or resistance created by the indwelling device 10 will promote proprioceptive neuromuscular facilitation and serve as a reminder to perform, and/or will facilitate the performance of, muscle-strengthening exercises (e.g., Kegal exercises) by the patient in whom the device 10 is indwelling. A more detailed description of proprioceptive neuromuscular facilitation is found in Sullivan, P. E., et al.: "An Integrated Approach To Therapeutic Exercise", published by Reston Publishing Co., Reston, Va., pages 161–183, the disclosure of which is expressly incorporated herein by reference.

With reference to FIGS. 1–3, the first embodiment of the device 10 comprises a generally elongate body 12 having a first end wall 14, a second end wall 16 and a pliable side wall 18. The first end wall 14 has a diameter $D_1$ which permits the device 10 to be easily inserted into the intended pelvic anatomical passageway (e.g., vagina, anus) but be large enough to capture, i.e., maintain, the device 10 at a desired position within the anatomical passageway. When inserted, the device 10 is in a rest mode (FIG. 2) wherein the pliable side wall 18 may have an inwardly curved configuration of a second diameter $D_2$ at it narrowest point. Such inwardly curved configuration of the side wall 18 may, for example, cause the device body 12 to have a hyperboloid or venturi-like configuration while in its rest mode.

An optional tube 20 extends longitudinally through the body 12 of the device 10 and forms a channel through which vaginal secretions may flow. A hollow, annular internal cavity 24 is defined within the device body 12, inboard of the pliable sidewall 18 and surrounding the tubular passageway 20.

A frusto-conical pressure-exerting member 22 is disposed within the generally annular internal cavity 24 formed within the body 12 of the device 10. A hollow central bore 26 extends longitudinally through the frusto-conical pressure-exerting member 22. As shown, the frusto-conical pressure-exerting member 22 is initially located in a rest mode position within the internal cavity 24, adjacent the first end wall 14 of the device body 12. The tube 20 passes through the central bore 26 formed in the pressure-exerting member 22. The pressure-exerting member 22 is slidably moveable in a downward direction, to an "exercise mode" position (FIG. 3) where at upper end (i.e., the larger diameter base) of the frusto-conical pressure exerting member 22 will exert radially outward pressure against the pliable side wall 18, thereby causing the inwardly curved region of the sidewall 18 to deform outwardly and to exert pressure against an adjacent region of the anatomical passageway (e.g., vagina or anus), as shown.

A motor housing 28 is mounted on the outer surface of the first end wall 14 of the body 12 and serves as an enclosure or housing for a small electric motor 30 along with a battery or power source 32 for powering the motor. An externally screw-threaded rotatable drive member 34 is connected to, and is driven by, the electric motor 30. Such screw-threaded rotatable drive member 34 extends through the first end wall 14 of the device body 12 and into an internally threaded first longitudinal bore 36 formed in the frusto-conical pressure-exerting member 22, as shown. A positioning dowel 38 is anchored to the underside of the motor housing 32 at a location opposite or spaced away from that of the rotatable threaded drive member 34. Such positioning dowel 38 extends through the first end wall 14 of the device body 12 and into a second longitudinal bore 40 which extends into the frusto-conical pressure-exerting member 22, as shown. In this regard, the motor 30 is initially operated in a first direction to cause the threaded rotatable drive member 34 to rotate in a first (e.g., counterclockwise) direction. Such rotation in the first direction will cause the threaded rotatable drive member 34 will rotatably withdraw from the threaded first longitudinal bore 36. Such retraction of the drive member 34 from the threaded first bore 36 will cause the frusto-conical pressure-exerting member 22 to move downwardly within the annular internal cavity 24 of the device body 12 from its initial rest mode position (FIG. 2) to its exercise mode position (FIG. 3). Concurrently with this downward travel of the frusto-conical resistance member, the positioning dowel 38 will slide partially out of the second bore 40, but will remain partially inserted into second bore 40 so as to hold the frusto-conical pressure-exerting member 22 firmly in the orientation shown in FIGS. 2 and 3.

When the frusto-conical pressure-exerting member 22 has descended to its exercise mode position, the patient will sense the exertion of pressure stretch or resistance against the vaginal or anal wall and/or adjacent muscles created by such operative positioning of the frusto-conical pressure-exerting member 22. The patient will be thereby reminded and compelled to volitionally perform the prescribed pelvic wall muscle exercises. Also, the pressure, stretch and/or resistance created by the operatively positioned pressure-exerting member 22 will improve the muscle-strengthening efficacy of such exercises by proprioceptive neuromuscular facilitation.

After a predetermined time (e.g., sufficient time for the patient to perform the prescribed muscle exercise) has expired, or upon delivery of other triggering input (e.g., a remote control signal), the electric motor 30 will drive the rotatable drive member 34 in a second direction (e.g., clockwise) such that the threaded drive member 34 will rotatably advance into the first threaded bore 36 of the frusto-conical pressure-exerting member 22, thereby causing the frusto-conical pressure-exerting member 22 to move from its "operative" position (FIG. 3) back to its "non-operative" position (FIG. 2). Again, the positioning dowel 38 will slide downwardly into the second longitudinal bore 40 of the frusto-conical pressure-exerting member 22 thereby maintaining the desired positioning of the frusto-conical pressure-exerting member 22 within the annular internal cavity 24 of the device body 12.

After the frusto-conical pressure-exerting member 22 has returned to its "non-operative" position (FIG. 2) the device 10 may remain in its rest mode and indwelling within the vagina V or anus A. Upon expiration of a predetermined time period or upon receipt of a triggering input signal, the motor 30 will again drive the rotatable threaded drive member 34 in the first direction so as to cause the frusto-conical pressure-exerting member 22 to once again descend to its "operative" position (FIG. 3), thus returning the device 10 to its exercise mode for an additional period of time.

The above-described sequence of events may be repeated on any prescribed schedule, or at any prescribed frequency or variable extension, so long as the device 10 remains indwelling within the vagina V or anus A. A small triggering and control apparatus, such as a timer, 53 may be mounted within the motor housing 58 and connected to the motor 60 to cause the motor to move the pressure-exerting member 22, up and down, on a predetermined time schedule. Alternatively, a remote control or telemetric switch or signal receiver may be utilized to receive remote control signals and to schedule the operation of the device by actuating or deactuate the movement of the pressure exerting member 22, as desired.

ii. Second Embodiment

By way of example, a second alternative embodiment of the device 10a is shown in FIGS. 4–6 which utilizes a different articulation mechanism to function in an analogous manner to that described in relation to FIGS. 1–3. In this second alternative embodiment, the device 10a comprises a device body 50 having first and second end walls 52, 54 and a pliable side wall 56. The pliable side wall 56 is bendable or otherwise alternately configureable in a first rest mode configuration (FIG. 5) wherein the sidewall 56 is inwardly curved (e.g., a hyperbolic or venturi-like shape) to a minimal diameter at its mid-region and a second exercise mode configuration (FIG. 6) wherein the side wall 56 is outwardly deformed or outwardly curved to an expanded diameter at its mid-region (FIG. 6).

A hollow interior cavity 57 is defined within the device body 50. A motor housing 58 is mounted on the first end wall 52 of the device body 50. The motor housing 52 serves as an enclosure or housing for a small electric motor 60 and battery 62. The battery 62 is connected to the electric motor 60 for the purpose of driving the electric motor 60.

A pressure-exerting assembly 64 is connected to the underside of the motor housing 58, and is disposed within the hollow interior cavity 57 of the device body 50. The pressure-exerting assembly 64 is operative to alternately move the side wall 56 of device body 50 between its rest mode configuration (FIG. 5) and its exercise mode configuration (FIG. 6). The preferred pressure-exerting assembly 64 generally comprises a central telescoping portion 66 and a plurality of hinged strut members 68 disposed about the central telescoping portion 66.

In particular, the central telescoping portion 66 of the pressure-exerting assembly 64 comprises a first rotatable shaft member 70 which is rotatably connected to the electric motor 60, and which is alternately rotatable in opposite directions (e.g., clockwise/counterclockwise) in accordance with forward or reverse rotation of the motor 60. The first shaft member 70 has an internally threaded longitudinal hollow bore extending through at least a portion thereof. A second solid shaft member 72, having an externally threaded outer surface is received within internally threaded hollow bore of the first shaft member 70 such that, when the first shaft member 70 is rotated in a first direction, the second shaft member 72 will advance longitudinally out of the end of the first shaft member 70 and when the first shaft member 70 is rotated in an opposite second direction, the second shaft member 72 will retract into the hollow bore of the first shaft member 70. In this regard, the central telescoping member 66 may alternate between a first rest mode length $L_1$ (FIG. 5) and a second exercise mode length $L_2$ (FIG. 6).

The bendable strut members 68 are disposed about the central telescoping member 66 such that, when the central telescoping member 66 shortens from its first length $L_1$ to its second length $L_2$, the bendable strut members 68 will bend and diverge at their hinged mid points 76, thereby exerting radially outward pressure against the side wall 56 to move from its rest mode configuration (FIG. 5) to its exercise mode configuration (FIG. 6).

The hinged strut members 68 are hingeably or bendably connected to non-rotating anchoring flanges 74, 75. The lower anchoring flange 74 is affixed to the end of the non-rotating second shaft member 72, as shown. The upper first flange member 75 is affixed to the underside of the motor housing 58 and is provided with a central aperture slightly larger in diameter than the outer diameter of the first shaft member 70 such that the first shaft member 70 extends through such aperture and remains freely rotatable while the first flange member 75 remains non-rotatably anchored to the motor housing 58.

In this regard, when it is desired to cause the device 10a to transition from its rest mode configuration (FIG. 5) to its exercise mode configuration (FIG. 6), the motor 60 will rotate the first shaft member 70 in a first direction (e.g., counter clockwise) such that the second shaft member 72 will telescopically retract into the bore of the first shaft member 70, thereby causing the central telescoping member 66 to shorten from its initial rest mode length $L_1$ to its exercise mode length $L_2$. Concurrently with such shortening of the central telescoping member 66, the hinged strut members 68 will bend at their central hinges 76 and will splay or diverge outwardly to exert radially outward pressure against the pliable side wall 56 of the device 10a, thereby forcing the side wall 56 from its inwardly curved configuration (FIG. 5a) to its outwardly curved or outwardly deformed configuration (FIG. 6).

Thereafter, when it is desired to return the device 10a to its rest mode configuration, the motor 60 will drive the first shaft member 70 in a second direction (e.g., clockwise) such that the second shaft member 72 will advance out of and longitudinally extend from the bore of the first shaft member 70, thereby causing the central telescoping member 66 to lengthen from its exercise mode length $L_2$ to its rest mode length $L_1$. Concurrently therewith, the hinged strut members 68 will move toward a straight, non-bent configuration such that the central hinge members 76 thereof will move radially inwardly so as to allow the pliable side wall 56 of the device to return from its outwardly curved exercise mode configuration (FIG. 6) to its inwardly curved rest mode configuration (FIG. 5).

As will be recognized, this second embodiment of the present invention additionally includes a timer or controller which functions to selectively cause the device 10 to go from a rest configuration to an operative configuration as desired. Additionally, in lieu of the plural articulating strut members 68 shown in FIG. 4, the plural spring members 68a may be utilized as depicted in FIG. 4a to provide an analogous expansion and contraction of the device 10. The spring members 68a may be formed of a metal or polymer material as desired.

iii. Third Embodiment

By way of further example, an alternative third embodiment of the invention is shown in FIGS. 7 and 8.

With reference to FIG. 7, the third embodiment of the device 10b comprises a device body 100 having a first end wall 102, a second end wall 104, and a side wall 106 having an inwardly curved (e.g., hyperboloid or venturi-like) configuration. A hollow interior space 114 is defined within the rigid side wall 106 and end walls 102, 104 of the device body 100. A pliable cylindrical membrane or balloon member 108 is mounted about the outer surface of the side wall 106 such that a fluid-tight inflation space 110 is formed between the inner surface of the pliable membrane or balloon member 108 and the outer surface of the rigid side wall 106.

A small battery-operated pump 112, including a battery therefore, is mounted within the interior space 114 of the device body in communication with an inflation inlet/outlet aperture 120 formed in the rigid sidewall 106 to permit passage of air or other inflation fluid into and out of the inflation space 110.

An inlet aperture 103 is formed in the top end wall 102 of the device body 100 to permit body secretions to flow through the device 10. An outlet aperture 105 is formed in the bottom end wall 104 to permit such secretions to flow out of the device 10.

When inserted in the vagina or anus, the body 100 of the device 10c will remain in its rest mode configuration such that the balloon or membrane 108 is inwardly curved to a diameter $D_2$ at it narrowest point, as shown in FIG. 7. Thereafter, when it is desired to cause the device 10c to exert radially outward pressure, stretch or resistance against the vaginal or anal wall and/or adjcent muscles, the pump 112 will be energized so as to pump air or other inflation fluid into the inflation space 110, thereby causing the balloon or membrane 108 to bulge outwardly to its configuration having a diameter $D_3$ at is widest point.

Thereafter, when it is desired to return the device 10c to its rest mode configuration, the pump 112 will be utilized to pump or vent inflation fluid from the inflation space 110 out of inflation inlet/outlet aperture 120, thereby allowing the balloon or membrane 108 to deflate, and to return to its original venturi-like rest mode configuration.

iv. Optional Vibrator and/or Heater Apparatus

In any embodiment of the invention, a vibrator apparatus or heater apparatus may optionally be mounted on or within the device to provide vibratory stimulation to the vaginal or anal wall and/or adjacent muscles to facilitate strengthening of the pelvic wall muscles and/or to serve as a sensory reminder to the patient to volitionally perform prescribe muscle-strengthening exercises. By way of example, FIG. 8 shows the device 10c of FIG. 7 having first and second optional vibrator and/or heater apparatus 122 mounted on the inner surface of the balloon or membrane 108. Such vibrator and/or heater apparatus may incorporate a small electrical motor or other vibrating device or conventional electric heater coupled to a small battery (not shown). The vibrator and/or heater apparatus 122 may be operated on a timed cycle, or may receive other triggering input which will cause the vibrator apparatus 122 to vibrate and/or heat when the device 10c is in its exercise mode configuration, but will allow the vibrator and/or heater apparatus 122 to remain non-vibrating and quiescent when the device 10c is in its rest mode configuration. Further, it will be recognized that the vibrator apparatus 122 may be used in lieu of the articulating motor drive mechanisms when desired.

It is to be understood that the individual elements and components of each above-described embodiment may be interchanged among and/or incorporated into any and all embodiments of the invention, even though certain elements or components may have been mentioned or described herein with respect certain embodiment(s) of the invention only.

It is to be further understood that various additions, deletions, modifications and alterations may be made to the above-described embodiments without departing from the intended spirit and scope of the present invention. Accordingly, it is intended that all such additions, deletions, modifications and alterations be included within the scope of the following claims.

What is claimed is:

1. A device which is adapted to be inserted into a pelvic anatomical passageway of a human being for facilitating the cyclical performance of pelvic muscle strengthening exercises, said device comprising:

a device body which is sized and configured for slidable insertion into said anatomical passageway and be retained therein, and which is alternately transitionable between:
   i) a rest mode configuration wherein said device body is adapted to exert no more than a baseline amount of pressure against a predetermined region of said anatomical passageway located adjacent said device; and,
   ii) an exercise mode configuration wherein said device body is adapted to exert more than said baseline amount of pressure against said predetermined region of said anatomical passageway; and, means for causing the device body to intermittently transition between said rest mode configuration and said exercise configuration at predetermined times.

2. The device of claim 1, wherein:

said device body has an upper end, a lower end, a pliable side and a longitudinal axis;

said pliable side wall of said device body being alternately configureable in:
   i) a rest mode configuration wherein said side wall is adapted to exert no more than a baseline pressure against a predetermined region of said anatomical passageway; and,
   ii) an exercise mode configuration wherein said side wall is adapted to exert more than said baseline pressure against said predetermined region of said anatomical passageway;

said device being adapted to be inserted into said anatomical passageway and operative therein to intermittently exert increased pressure against said predetermined region of said anatomical passageway to facilitate performance of pelvic muscle strengthening exercises by the human being.

3. The device of claim 1 wherein said anatomical passageway is the vagina and wherein said device is sized and configured for intravaginal insertion.

4. The device of claim 1 wherein said anatomical passageway is the anus and said device is sized and configured for intra-anal insertion.

5. A method for facilitating the performance of pelvic muscle strengthening exercises to treat incontinence in a patient, said method comprising the steps of:

a) providing a device which is adapted to be inserted into and retained within a pelvic anatomical passageway of a patient, said device comprising:

a device body which is configured for slidable insertion into said anatomical passageway;

said device body being alternately transitionable between a rest mode configuration wherein said device exerts no more than a base line amount of pressure against a predetermined region of said anatomical passageway located adjacent said device, and an exercise mode configuration wherein said device exerts more than said base line amount of pressure against said predetermined region of said anatomical passageway;

b) inserting said device body into said anatomical passageway;
   c) causing said device body to remain in its rest mode configuration for a first predetermined period of time;
   d) causing said device body to transition to its exercise mode configuration for a second predetermined period of time;
   e) causing said device body to return to its rest mode configuration.

6. (Amended) The method of claim 5 further comprising the step:

f) consecutively repeating steps c, d and e while said device remains indwelling within said anatomical passageway.

7. The method of claim 5 wherein said anatomical passageway is the vagina and step b of said method comprises inserting said device body into the vagina.

8. The method of claim 5 wherein said anatomical passageway is the anus and step b of said method comprises inserting said device body into the anus.

9. A device adapted to treat urinary and/or fecal incontinence by promoting proprioceptive neuromuscular facilitation of a user, said device comprising:

a body member sized and configured for slidable insertion into and retention within an anatomical passageway of said user; and means carried by said body member for periodically exerting a force on said anatomical passageway, said force providing sufficient stimulus to said user to effectuate said proprioceptive neuromuscular facilitation of said user.

10. The device of claim 9 wherein said means comprises an expanding region formed within said body member.

11. The device of claim 9 wherein said means further comprises means for regulating the duration of said force.

12. A device which is adapted to be inserted into a pelvic anatomical passageway of a human being for facilitating the performance of pelvic muscle strengthening exercises, said device comprising:

a) a device body which is sized and configured for slidable insertion into said anatomical passageway and be retained therein, and which is alternately transitionable between:
   i) a rest mode configuration wherein said device body is adapted to exert no more than a baseline amount of pressure against a predetermined region of said anatomical passageway located adjacent said device; and
   ii) an exercise mode configuration wherein said device body is adapted to exert more than said baseline amount of pressure against said predetermined region of said anatomical passageway; and, b) means for causing the device to transition between said rest mode configuration and said exercise configuration at predetermined times, said means comprising:
   i) an electric motor;
   ii) a batter connected to said electric motor for powering said electric motor; and
   iii) a timer apparatus connected to said electric motor and operative to cause said electric motor to alternately drive said device body between said rest mode configuration and said exercise mode configuration on a predetermined schedule.

13. The device of claim 12 wherein said means for causing the device to transition between said rest mode configuration and said exercise mode configuration further comprises an intermittent pressure exerting apparatus, said intermittent pressure exerting apparatus comprising:

a frusto-conical member slideably disposed within said device body in contact with said pliable side wall;

said frusto-conical member having a first end of a first diameter and a second end of a second diameter, said second end being larger in diameter than said first end;

said frusto-conical member being slidably shiftable, back and forth, between:
- i) said rest mode position wherein the pliable side wall of said device body is allowed to remain in its rest mode configuration; and,
- ii) an exercise mode position wherein said second end of said frusto-conical member exerts outwardly deforming pressure against a portion of said pliable side wall to cause that portion of said pliable sidewall to deform in a radially outward direction, said sidewall being thereby transitioned to its exercise mode configuration.

14. The device of claim 12 wherein said means for causing the device to transition between said rest mode configuration and said exercise mode configuration further comprises an intermittent pressure exerting apparatus, said intermittent pressure exerting apparatus comprising:

a plurality of hinged strut members disposed within said device body and connected to a telescoping central longitudinal member which is adapted to be alternately lengthened and shortened so as to cause said hinged strut members to alternatively move between:
- i) said rest mode position wherein said hinged strut members are disposed within said device body such that said pliable side wall may remain in its rest mode configuration; and,
- ii) an exercise mode position wherein said hinged strut members undergo bending at their hinges so as to exert radially outward deforming pressure against said pliable side wall such that said sidewall will thereby transition to its exercise mode configuration.

15. The device of claim 12 wherein said means for causing the device to transition between said rest mode configuration and said exercise mode configuration further comprises an intermittent pressure exerting apparatus, said intermittent pressure exerting apparatus comprising:

at least one inflatable space formed inboard of said pliable side wall such that the passage of a space occupying fluid into and out of said inflation space will cause said pliable side wall to alternately move between its rest mode configuration and its exercise mode configuration.

16. The device of claim 12 further comprising:

a housing located on one end of said device body; and, wherein said motor and said battery are located within said housing.

17. The device of claim 16 wherein said timer apparatus is also located within said housing.

18. A device which is adapted to be inserted into a pelvic anatomical passageway of a human being for facilitating the cyclical performance of pelvic muscle strengthening exercises, said device comprising:

a) a device body which is sized and configured for slidable insertion into said anatomical passageway and be retained therein, said device body having an upper end, a lower end, a pliable side wall and a longitudinal axis, said pliable side wall being alternately configurable in:
- i) a rest mode configuration wherein said side wall is adapted to exert no more than the baseline pressure against a predetermined region of said anatomical passageway;
- ii) an exercise mode configuration wherein said side wall is adapted to exert more than said baseline pressure against said predetermined region of said anatomical passageway; and b) means for causing the device body to transition between said rest mode configuration and said exercise mode configuration at predetermined times, said means being coupled with a timer apparatus for causing said means to alternately transition said device body between said rest and exercise mode configurations at said predetermined timed intervals; and c) wherein said device is adapted to be inserted into said anatomical passageway and operative therein to intermittently exert increased pressure against said predetermined region of said anatomical passageway to facilitate performance of said pelvic muscle strengthening exercises by the human being.

19. A device which is adapted to be inserted into a pelvic anatomical passageway of a human being for facilitating the cyclical performance of pelvic muscle strengthening exercises, said device comprising a device body which is sized and configured for slidable insertion into said anatomical passageway and be retained therein, said device body having an upper end, a lower end, a pliable side wall and a longitudinal axis;

a) said pliable side wall of said device body being alternately configurable in:
- i) a rest mode configuration wherein said side wall is adapted to exert no more than the baseline pressure against a predetermined region of said anatomical passageway;
- ii) an exercise mode configuration wherein said side wall is adapted to exert more than said baseline pressure against said predetermined region of said anatomical passageway; and b) means for causing the device body to transition between said rest mode configuration and said exercise mode configurations at predetermined times, said means being coupled with a remote controlled triggering apparatus operative to receive remote control signals and to cause said device body to assume said exercise mode configuration when said remote control signals are received; and c) wherein said device is adapted to be inserted into said anatomical passageway and operative therein to intermittently exert increased pressure against said predetermined region of said anatomical passageway to facilitate performance of said pelvic muscle strengthening exercises by the human being.

20. A device which is adapted to be inserted into a pelvic anatomical passageway of a human being for facilitating the cyclical performance of pelvic muscle strengthening exercises, said device comprising:

a device body which is sized and configured for slidable insertion into said anatomical passageway and be retained therein, and which is alternately transitionable between:
- i) a rest mode configuration wherein said device body is adapted to exert no more than a baseline amount of pressure against a predetermined region of said anatomical passageway located adjacent said device; and, ii) an exercise mode configuration wherein said device body is adapted to exert more than said baseline amount of pressure against said predetermined region of said anatomical passageway; and, means for causing the device body to intermittently transition between said rest mode configuration and said exercise configuration at predetermined times; and a vibrator apparatus coupled to said device body for causing at least a portion of said device body to vibrate.

21. The device of claim 20, wherein said vibrator apparatus is commonly controlled with said intermittent pressure exerting apparatus such that said vibrator apparatus and said intermittent pressure exerting apparatus will be actuated and deactuated concurrently with one another.

22. A method of treating incontinence in a patient, said method comprising the steps of:

a) providing a device which is insertable into and retained within a pelvic anatomical passageway of a patient, said device comprising:
   i) a device body which is configured for slidable insertion into said anatomical passageway;
   ii) said device being ultimately transitionable between a rest mode configuration wherein said device exerts no more than a baseline amount of pressure against a predetermined region of said anatomical passageway located adjacent said device, and an exercise mode configuration wherein said device exerts more than said baseline amount of pressure against said predetermined region of said anatomical passageway;
   iii) means for controlling the transition of said device body between said rest mode configuration and said exercise mode configuration at predetermined times;

b) inserting said device body into said anatomical passageway;

c) causing said device body to remain in its rest mode configuration for a first predetermined period of time;

d) causing said device body to transition to its exercise mode configuration for a second predetermined period of time; and e) causing said device body to return to its rest mode configuration; and f) performing steps c, d and e, said steps c, d and e being performed automatically by said means for controlling said transition of said device body between said rest mode configuration and said exercise mode configuration.

23. The method of claim 22 wherein the means for controlling the transition of the device body provided in step a comprises a programmable timer apparatus;

and, wherein said method further comprises the step:

f) performing steps c, d, and e, said step c, d, and e, are carried out by programming said timer apparatus to cause said device body to transition between its rest mode configuration and its exercise configuration on a predetermined schedule.

24. The method of claim 22 wherein step d, further comprises:

causing said device body to vibrate while in said exercise mode configuration.

25. A device adapted to treat urinary and/or fecal incontinence comprising:

a body member sized and configured for slidable insertion into and retention within an anatomical passageway of a user; and a vibrator carried by said body member for periodically exerting a force on said anatomical passageway to promote proprioceptive neuromuscular facilitation of the user.

26. A device adapted to treat urinary and/or fecal incontinence comprising:

a body member sized and configured for slidable insertion into and retention within an anatomical passageway of a user; and a heater carried by said body member for periodically exerting a force on said anatomical passageway to promote proprioceptive neuromuscular facilitation of the user.

27. A device adapted to be inserted into a pelvic anatomical passageway of a human being for promoting physical sensation therewithin to signal the performance of the pelvic muscle strengthening exercises, said device comprising:

a) a device body sized and configured to be slidably inserted and frictionally retained within said anatomical passageway, said device body being alternately transitionable between:
   i) a rest mode configuration wherein said device body is adapted to exert no more than a first baseline amount of pressure against a predetermined region of said anatomical passageway located adjacent said device; and
   ii) an exercise mode configuration wherein said device body is adapted to exert a second baseline amount of pressure against said predetermined region of said anatomical passageway, said second baseline amount of pressure being greater than said first baseline amount of pressure and of sufficient force to promote physical sensation within said anatomical passageway; and b) means for causing said device body to cyclically transition between said rest mode configuration and said exercise mode configuration at predetermined times.

28. A device adapted to be inserted into a pelvic anatomical passageway of a human being to remind the user to perform pelvic muscle strengthening exercises, said device comprising:

a) a device body sized and configured to be slidably inserted and frictionally retained within said anatomical passageway, said device body being alternately transitionable between:
   i) a rest mode configuration wherein said device body is adapted to exert no more than a first baseline amount of pressure against a predetermined region of said anatomical passageway located adjacent said device; and
   ii) an exercise mode configuration wherein said device body is adapted to exert a second baseline amount of pressure against said predetermined region of said anatomical passageway, said second baseline amount of pressure being greater than said first baseline amount of pressure and of sufficient force to promote physical sensation within said anatomical passageway and of sufficient strength to remind the user to perform said pelvic muscle strengthening exercises; and b) means for causing said device body to cyclically transition between said rest mode configuration and said exercise mode configuration at predetermined times.

* * * * *